United States Patent [19]

Slungaard

[11] Patent Number: 5,674,489
[45] Date of Patent: Oct. 7, 1997

[54] METHOD TO ENHANCE THROMBOMODULIN APC GENERATION USING CATIONIC PROTEINS

[75] Inventor: Arne Slungaard, St. Paul, Minn.

[73] Assignee: Regents of the University of Minnesota, Minneapolis, Minn.

[21] Appl. No.: 698,329

[22] Filed: Aug. 15, 1996

Related U.S. Application Data

[62] Division of Ser. No. 121,226, Sep. 14, 1993, Pat. No. 5,585,095.

[51] Int. Cl.$^6$ .................. A61K 38/48; A61K 38/02; A61K 38/16; A61K 38/36
[52] U.S. Cl. .................. 424/94.64; 514/2; 514/8; 514/12
[58] Field of Search .................. 424/94.64; 514/2, 514/8, 12

[56] References Cited

U.S. PATENT DOCUMENTS

| | | | |
|---|---|---|---|
| 5,086,164 | 2/1992 | Maione | 530/324 |
| 5,112,946 | 5/1992 | Maione | 530/324 |
| 5,196,322 | 3/1993 | Bang et al. | 435/69.8 |
| 5,204,321 | 4/1993 | Cook et al. | 514/2 |

FOREIGN PATENT DOCUMENTS

| | | |
|---|---|---|
| 0412841A1 | 2/1991 | European Pat. Off. . |
| 0443875A2 | 8/1991 | European Pat. Off. . |
| 0458903 | 12/1991 | European Pat. Off. . |
| 2671973 | 7/1992 | France . |
| WO90/10081 | 9/1990 | WIPO . |
| WO91/15514 | 10/1991 | WIPO . |
| WO93/09807 | 5/1993 | WIPO . |

OTHER PUBLICATIONS

Marie–Claude Bourin, et al., "Isolation and Characterization of the Glycosaminoglycan Component of Rabbit Thrombomodulin Proteoglycan", *J. of Biol. Chem.*, 256, 15424–15431, (1990).

Marie–Claude Bourin, et al., "Relationship Between Anticoagulant Activities and Polyanionic Properties of Rabbit Thrombomodulin", *J. of Biol. Chem.*, 263, 8044–8052, (1988).

Thomas F. Deuel, et al., "Amino Acid Sequence of Human Platelet Factor 4", *Proc. Natl. Acad. Sci. USA*, 74, 2256–2258, (1977).

William A. Dittman, et al., "Structure and Function of Thrombomodulin: A Natural Anticoagulant", *Blood*, 75, 329–336, (1990).

Naomi L. Esmon, et al., "Isolation of a Membrane–bound Cofactor for Thrombin–catalyzed Activation of Protein C", *J. of Biol. Chem.*, 257, 859–864, (1982).

Charles T. Esmon, "The Roles of Protein C and Thrombomodulin in the Regulation of Blood Coagulation", *J. of Biol. Chem.*, 264, 4743–4746, (1989).

Charles B. Glaser, et al., "Oxidation of a Specific Methioninein Thrombomodulin by Activated Neutrophil Products Blocks Cofactor Activity", *J. Clin. Invest.*, 90, 2565–2573, (1992).

John H. Griffin, et al. "Deficiency of Protein C in Congenital Thrombotic Disease", *J. Clin. Invest.*, 68, 1370–1373, (1981).

Shinchiro Kurosawa, et al., "Proteolytic Formation and Properties of Functional Domains of Thrombomodulin", *J. of Biol. Chem.*, 262, 2206–2212, (1987).

R. Michalski, et al., "Neutralization of Heparin in Plasma by Placelet Factor 4 and Protamine Sulphate", *Brit. J. of Haematology*, 38, 561–571, (1978).

Katsuhiko Nawa, et al., "Presence and Function of Chondroitin–4–Sulfate on Recombinant Human Soluble Thrombomodulin", *Biochemical and Biophysical Res. Comm.*, 171, 729–737, (1990).

Katsuhiko Nawa, et al., "The Glycosaminoglycan of Recombinant Human Soluble Thrombomodulin Affects Antithrombotic Activity in a rat Model of Tissue Factor–Induced Disseminated Intravascular Cagulation", *Thrombosis and Hemostasis*, 66, 366–370, (1992).

John F. Parkinson, et al., "Recombinant Human Thrombomodulin", *Biochem. J.*, 283, 151–157, (1992).

John F. Parkinson, et al., "Stable Expression of A Secretable Deletion Mutant of Recombinant Human Thrombomodulin in Mammalian Cells", *J. of Biol. Chem.*, 265, 12602–12610, (1990).

K. T. Preissner, et al., "Domain Structure of the Endothelial Cell Receptor Thrombomodulin as Deduced from Modulation of Its Anticoagulant Functions", *J. Biol. Chem.*, 265, 4915–4922, (1990).

Uri Seligsohn, et al., "Homozygous Protein C Deficiency Manifested by Massive Venous Thrombosis in the Newborn", *New Engl. J. of Medicine*, 310, 559–562 (1984).

Arne Slungaard, et al., "Bromide–dependent Toxicity of Eosinophil Peroxidase for Endothelium and Isolated Working Rat Hearts: A Model for Eosinophilic Endocarditis", *J. Exp. Med.*, 173, 117–126, (1991).

Arne Slungard, et al., "Eosinophil Cationic Granule Proteins Impair Thrombomodulin Function", *J. Clin. Invest.*, 91, 1721–1730, (1993).

F. B Taylor, et al., "Protein C Prevents the Coagulopathic and Lethal Effects of *Escherichia coli* Infusion in the Baboon", *J. Clin. Invest.*, 79, 918–925, (1987).

(List continued on next page.)

*Primary Examiner*—Robert A. Wax
*Assistant Examiner*—Kawai Lau
*Attorney, Agent, or Firm*—Schwegman, Lundberg, Woessner & Kluth, P.A.

[57] ABSTRACT

A method of inhibiting blood coagulation in a patient is provided. This method involves administering to the patient an effective anticoagulant amount of a cationic protein; wherein the cationic protein has an isoelectric point of at least about 7.4, and is capable of enhancing the production of activated protein C by a thrombomodulin-thrombin complex by a factor of at least about two. A particularly preferred cationic protein is purified Platelet Factor 4.

16 Claims, 2 Drawing Sheets

OTHER PUBLICATIONS

Majorie B. Zucker, et al., "Platelet Factor 4: Production, Structure, and Physiologic and Immunologic Action", *Soc. for Exp. Biology and Med.*, 198(2), 693–702, (1991).

Bourin, M.-C. et al. (1988) "Relationship between anticoagulant activities and polyanionic properties of rabbit thrombomodulin" J. Biol. Chem. 263(17):8044–8052 Jun. 1988.

Preissner, K. T. et al. (1990) "Domain structure of the endothelial cell receptor thrombomodulin as deduced from modulation of its anticoagulant functions" J. Biol. Chem. 265(9):4915–1922 Mar. 1990.

METHOD TO ENHANCE THROMBOMODULIN APC GENERATION USING CATIONIC PROTEINS

This is a division of application Ser. No. 08/121,226, filed Sep. 14, 1993 now U.S. Pat. No. 5,585,095.

BACKGROUND OF THE INVENTION

The control of bleeding and clotting are extremely important in medical and surgical procedures. Protein C, a vitamin K-dependent plasma protein, is of major physiological importance in the control of bleeding. Protein C exists in two major forms, i.e., an inactive or nascent form and an active form. Active protein C ("APC") is a natural anticoagulant formed upon the proteolytic activation of protein C. This proteolytic activation is catalyzed in the blood by a thrombomodulin-thrombin complex.

Thrombin is an enzyme that has significant procoagulant activity. For example, it cleaves fibrinogen to form soluble fibrin, it activates platelets, and it converts the clotting cofactors V and VIII to their activated forms Va and VIIIa. Although it can activate protein C to form the natural anticoagulant APC, this activation is inhibited by physiological $Ca^{2+}$ concentrations. Thrombin, however, can be inactivated by antithrombin (AT III).

Thrombomodulin (TM) is a 105 kD anionic transmembrane glycoprotein expressed on the surface of endothelial cells. Thrombomodulin strongly binds [$K_d$ 0.5 nM] the circulating enzyme thrombin (THR) and thereby dramatically alters the functional properties of thrombin. The complexation of THR by TM alters its substrate specificity so that the fibrinogen-cleaving activity of THR and the activation of platelets are curbed, i.e., attenuated. Also, the inactivation of thrombin by antithrombin is enhanced by this complexation. Furthermore, the altered substrate specificity of THR results in a significant acceleration of its proteolytic activation of circulating protein C to activated protein C, particularly in the presence of physiological $Ca^{2+}$. APC, in turn, is a powerful anticoagulant serine protease which, in conjunction with protein S, terminates the procoagulant activity of Factors Va and VIIIa. See, C. T. Esmon, *J. Biol. Chem.*, 264, 4743–4746 (1989), and W. A. Dittman et al., *Blood*, 75, 329–336 (1990). Thus, TM-dependent APC generation is crucial to the regulation of clotting. This is shown by the fulminant lethal thrombosis occurring in newborns with severe homozygous deficiencies of protein C, and the pronounced venous and arterial clotting diathesis that plagues some individuals heterozygous for protein C deficiency. See, U. Seligsohn et al., *N. Engl. J. Med.*, 310, 559 (1984), and J. H. Griffin et al., *J. Clin. Invest.*, 68, 1370 (1981).

In sum, the procoagulant activities of thrombin are inhibited by thrombomodulin (TM) in three distinct ways. It promotes the activation of protein C by thrombin, which can be referred to as protein C activation cofactor activity. It promotes the inactivation of thrombin by antithrombin, which can be referred to as antithrombin-dependent anticoagulant activity. Finally, it prevents the cleavage of fibrinogen by thrombin, which can be referred to as direct anticoagulant activity.

The complete TM molecule is quite anionic (pI≈4), in part because of extensive post-translational glycation of the large extracellular domain of TM with an unusual hypersulfated, chondroitin E-like glycosaminoglycan (GAG) moiety. This bulky polyanionic domain strongly influences the three anticoagulant functions of TM. See, M.-C. Bourin et al., *J. Biol. Chem.*, 265, 15424–15431 (1990), K. Nawa et al., *Biochem. Biophys. Res. Commun.*, 171, 729–737 (1990), K. T. Preissner et al., *J. Biol. Chem.*, 265, 4915–4922 (1990), and J. F. Parkinson et al., *Biochem. J.*, 283, 151–157 (1992).

The interaction of highly (pI>11) cationic eosinophil-specific granule proteins with anionic TM has also been examined. It was believed that these toxic cationic proteins (major basic protein, eosinophil peroxidase, eosinophil cationic protein, and eosinophil-derived neurotoxin) might bind to TM through electrostatic interactions and impair its functions. See, A. Slungaard et al., *J. Clin. Invest.*, 91, 1721–1730 (1993). Several such proteins, including major basic protein (MBP), were found to potently inhibit ($IC_{50}$ of 1–2 μM) the capacity of endothelial cell TM to generate APC. MBP also inhibited APC generation by purified, soluble rabbit TM with an $IC_{50}$ of 100 nM (roughly 1 μg/ml). This inhibition was reversed by polyanions such as chondroitin sulfate E or heparin. The interaction between MBP and TM occurred with the large O-linked GAG moiety because a recombinant TM polypeptide comprising the soluble extracellular domain including the GAG was strongly inhibited by MBP whereas its counterpart lacking the GAG was not so inhibited. Thus, eosinophil cationic granule proteins potently inhibited anticoagulant activities of the glycosylated (GAG+) form of TM, thereby suggesting a potential mechanism to explain the pronounced thromboembolic diathesis that characterizes hypereosinophilic conditions. Based on these experiments with the eosinophil cationic proteins, it has been predicted that Platelet Factor 4 and other cationic proteins might similarly inhibit TM function and thereby promote clotting in the presence of activated platelets.

The present invention is based on the discovery that Platelet Factor 4 and other relatively nontoxic cationic proteins do not function as do the highly toxic eosinophil cationic granule proteins. Thus, the present invention provides a composition containing cationic proteins that promotes the inhibition of blood coagulation. Such compositions find utility in a variety of clinical settings including treatment of myocardial infarction, pulmonary embolism, cerebrovascular disease and the like.

SUMMARY OF THE INVENTION

The present invention provides a method of inhibiting blood coagulation in a patient. As used herein "patient" refers to mammals such as primates, including humans, sheep, horses, cattle, pigs, dogs, cats, rats, and mice. This method involves administering to the patient an effective amount of a cationic protein; wherein the cationic protein has an isoelectric point of at least about 7.4, and enhances the production of activated protein C by a thrombomodulin-thrombin complex by a factor of at least about two. A particularly preferred cationic protein is purified Platelet Factor 4, whether purified naturally occurring Platelet Factor 4 or purified recombinant Platelet Factor 4. Although a variety of cationic proteins can be used, other particularly preferred embodiments of the method include administering poly-L-lysine or protamine sulfate as the cationic protein. Preferably, the method involves administering an effective anticoagulant mount of a thrombomodulin preparation and/or thrombin in combination with the cationic protein for particularly effective results.

The present invention also provides a method of inhibiting blood coagulation in a medium, e.g., a sample of whole blood, as well as a method of producing activated protein C (APC) either in a patient or in vitro in a medium such as whole blood. These methods involve adding an effective mount of a cationic protein as described above, preferably PF4, either alone or in combination with thrombomodulin and/or thrombin. As used herein, an "effective amount" is an amount effective to inhibit coagulation, or generate large amounts of APC that can be used for the treatment of various disorders, such as septic shock for example.

The present invention is also directed to anticoagulant compositions containing a cationic protein as described above, preferably PF4, in combination with thrombomodulin, thrombin, or both thrombomodulin and thrombin. Although the compositions containing a cationic protein such as PF4 alone are effective anticoagulants, those containing a cationic protein and thrombomodulin are even more effective anticoagulants.

DETAILED DESCRIPTION

The present invention provides methods for inhibiting blood coagulation using cationic proteins that enhance APC generation from a thrombomodulin-thrombin complex, and suitable pharmaceutical compositions containing the cationic proteins. Specifically, the present invention provides methods for inhibiting blood coagulation in a patient upon the administration of an effective anticoagulant amount of a cationic protein that has an isoelectric point of at least about 7.4 and enhances APC generation. The present invention also provides methods for enhancing the production of APC by administering such a cationic protein to a patient, or by adding it to a medium containing a thrombomodulin-thrombin complex (or sufficient TM and THR to initiate the production of APC), such as whole blood, blood plasma, and other biological samples in which blood coagulation is undesirable. In this way, whole blood, plasma samples, and other biological samples can be stored for longer periods of time with a reduced incidence of blood clotting. Also, large amounts of APC can be generated in vivo, or in vitro and harvested, for use in the treatment of disorders requiring infusion of large amounts of APC, such as septic shock (see, Taylor et al., *J. Clin. Invest.*, 79, 918–925 (1987)).

Suitable cationic proteins for use in the methods and compositions of the present invention: (1) have a net positive charge when incorporated into a sample of blood, i.e., they have an isoelectric point of at least about 7.4; and (2) enhance the production of APC by a thrombomodulin-thrombin complex by a factor of at least about two, according to the screening test outlined below. Briefly, this screening test involves incubating a cationic protein, a full-length rabbit TM preparation, protein C, physiologic $Ca^{2+}$, and THR in a Tris (tris(hydroxymethyl)aminomethane) and NaCl buffer for about 10 minutes, quenching the reaction with AT III and EDTA, and measuring the amount of APC produced. The cationic proteins that show at least a two-fold increase in APC generation preferably include relatively nontoxic proteins, such as, for example, platelet factor 4 (PF4), poly-L-lysine (preferably of a molecular weight of at least about 4000–15,000), protamine sulfate, β-thromboglobulin, lysozyme, poly-L-arginine (preferably of a molecular weight of at least about 5000–15,000), polyhistidine (preferably of a molecular weight of at least about 5000–15,000), and vitronectin peptide. As used herein, "relatively nontoxic" refers to proteins that, unlike the eosinophil cationic proteins, do not typically kill cells at concentrations of less than about $10^{-4}$ molar using a $^{51}Cr$ release assay employing human umbilical vein endothelial cells (see, Slungaard et al., *J. Exp. Med.*, 173, 117–126 (1991)), which is incorporated herein by reference. These include a wide variety of "non-eosinophil-specific granule" proteins.

More preferred cationic proteins for use in the methods and compositions of the present invention are capable of binding to heparin, i.e., they are heparin-binding cationic proteins. Most preferably, the cationic proteins are selected from a group consisting of poly-L-lysine of a molecular weight of about 4000–15,000, promtamine sulfate, and platelet factor 4 (PF4). Of this most preferred group, PF4 is particularly preferred at least because of its potency, lack of toxicity, and availability for human administration.

Platelet factor 4 (PF4) is a moderately cationic (pKa 7.8) and hydrophobic major protein constituent (20 µg/$10^9$ platelets) of platelet α-granules, which are released during platelet aggregation in plasma, i.e., when platelets are physiologically activated by thrombin (THR). See, M. B. Zucker et al., *Proc. Soc. Exp. Biol. Med.*, 198, 693–702 (1991). PF4 is typically found in human plasma at concentrations of 5–20 ng/ml, has a molecular weight of 7.8 kD, and has an exceptionally high affinity for heparin, requiring 1.5–2M NaCl to dislodge it from a Sepharose-heparin affinity column as opposed to 0.5M NaCl required for two other major constituents of α-ganules: β-thromboglobulin (and its related proteins) and thrombospondin.

Platelet Factor 4 (PF4) is capable of binding to endothelial cells, and has been shown to be useful in the inhibition of endothelial cell proliferation and angiogenic diseases resulting therefrom. See, U.S. Pat. Nos. 5,086,164 (issued Feb. 4, 1992) and 5,112,946 (issued May 12, 1992). It has also been shown to reverse the effect of heparin, an anticoagulant, thereby promoting clotting. See, for example, Michalski, *Brit. J. Haematol.*, 38, 561–571 (1978). Furthermore, PF4 can be used to neutralize high levels of circulating heparin after heparin has been administered in a medical procedure, thereby restoring a patient's normal coagulation status. See, U.S. Pat. No. 5,204,321 (issued Apr. 20, 1993). Thus, prior to the present invention, those skilled in the art would have been led away from using PF4 as an anticoagulant.

PF4, as well as the other cationic proteins discussed above, are typically provided in their purified form, i.e., a form that is substantially free of other proteins, lipids, and carbohydrates with which they are typically associated. A purified protein preparation will generally yield a single major band on a polyacrylamide gel for each subunit of desired protein, e.g., PF4. Preferably, the purified cationic protein used in the methods and compositions of the present invention are pure as judged by amino terminal amino acid sequence analysis. The purified cationic protein can be naturally occurring, synthetic, i.e., chemically produced, or recombinant, i.e., biologically cloned. A recombinant from of PF4 can be produced in *E. coli* according to the method outlined in U.S. Pat. No. 5,204,321 (Cook et al., issued Apr. 20, 1993). Preferably, the cationic protein is naturally occurring, i.e., isolated, or recombinant. More preferably it is naturally occurring. It can be a full length, i.e., whole, protein or a peptide fragment thereof. As used herein, a "fragment" refers to a portion of a longer amino acid sequence. The purified cationic protein can be an analog, i.e., mutant, of the naturally occurring protein. As used herein, an "analog" or "mutant" refers to a cationic protein that is substantially the same as another but which has different amino acids at certain locations in the amino acid sequence. The cationic protein, fragment, or mutant thereof can also be chemically modified to produce an adduct that can be used in the methods and compositions of the present invention. Additionally, routants and adducts of peptide fragments, whether produced by isolation, synthetic, or recombinant techniques, can be used in the methods and compositions of the present invention. The mutants, adducts, and fragments are useful as long as they retain anticoagulant activity, preferably substantially the same anticoagulant activity as the original cationic protein. That is, the modifications of the proteins, e.g., mutants, adducts, and fragments, are useful in the methods and compositions of the present invention as long as they enhance the production of APC by a thrombomodulin-thrombin complex by a factor of at least about two according to the screening test outlined below.

Although preferred embodiments of the methods and compositions of the present invention require a cationic protein that is capable of binding heparin, specific modifications of PF4 that do not bind heparin and/or are not cationic, can be used as long as they enhance the production of APC by a thrombomodulin-thrombin complex by a factor of at least about two, according to the screening test outlined below. For example, it is believed that a PF4 mutant that lacks heparin binding activity can be used. One such mutant is known as rPF4-241 which was created by mutagenesis of a synthetic PF4 gene whereby the DNA sequence encoding the four lysine residues near the carboxy terminus of PF4 were converted to a sequence encoding two Gln-Glu couplets. This mutant is described in U.S. Pat. No. 5,086,164 (Maione et al., issued Feb. 4, 1992). Also, it is believed that a PF4 adduct that lacks heparin binding activity can be used. One such adduct was prepared by modifying the free amino groups of rPF4 with fluorescein-isothiocyanate. This adduct is described in U.S. Pat. No. 5,112,946 (Maione, issued May 12, 1992).

Preferably, and advantageously, a cationic protein or modifications thereof as described above are used in the methods and compositions of the present invention in combination with a thrombomodulin (TM) preparation to further enhance the generation of APC and inhibit blood coagulation. Alternatively, the cationic protein can be used alone, in combination with a different cationic protein or modification thereof, in combination with protein C, or in combination with thrombin (THR), a substance known to activate APC generation by endogenous or exogenous forms of TM, to further enhance APC generation. In such situations, endogenous forms of TM are utilized. That is, it is understood that if a cationic protein is administered alone, the medium to which it is administered, such as whole blood or a patient, contains sufficient TM and THR to form a TM-THR complex in situ and initiate the natural production of APC. However, if either TM or THR is present in a low concentration such that little or no TM-THR complex is formed in situ, then either or both of these can be added either simultaneously or sequentially with the cationic protein. Significant advantage is realized upon the administration of a cationic protein, particularly PF4, in combination with thrombomodulin due to a profound enhancement of the production of APC.

In applications in which TM, THR, and/or protein C are used, they are administered in an effective anticoagulant amount. These amounts can be determined by one of skill in the art. They can be administered simultaneously or sequentially. Also included within the scope of the present invention include pharmaceutical compositions of a cationic protein as described above and a thrombomodulin preparation and/or thrombin.

Thrombomodulin (TM) is typically provided in its purified form, i.e., a form that is substantially free of other proteins, lipids, and carbohydrates with which it is typically associated. A purified TM preparation will generally yield a single major band on a polyacrylamide gel. Preferably, the purified TM used in the methods and compositions of the present invention is pure as judged by amino terminal amino acid sequence analysis. The purified TM can be naturally occurring, synthetic, or recombinant. It can be a full length, i.e., whole, protein or a peptide fragment thereof. The purified TM can be an analog, i.e., mutant, of the naturally occurring protein that confers a beneficial property. For example, to provide a TM that is resistant to oxidation a mutant comprising the extracellular domain (amino acids 1–497) containing a 388 MET to LEU substitution can be used, as well as GAG+ and GAG– variants of this mutant. The TM protein, fragment, or mutant thereof can also be chemically modified to produce an adduct that can be used in the methods and compositions of the present invention. For example, GAG+ forms of TM can be converted to GAG– forms by chemical modification. Additionally, mutants and adducts of peptide fragments, whether produced by isolation, synthetic, or recombinant techniques, can be used in the methods and compositions of the present invention. The TM preparation can also be a naturally occurring or transfected construct of TM expressed in endothelial or other mammalian cells. For example, wild type and 388 MET to LEU mutant forms of TM have been expressed in CHL human melanoma and Chinese hamster ovary cell lines. GAG+ and GAG– forms of TM as well as other derivatives of thrombomodulin are disclosed in European Patent Application 458,903 (Morser et al., published Dec. 4, 1991); European Patent Application 527,821 (Glaser et al., published Feb. 24, 1993); Parkinson et al., *J. Biol. Chem.*, 265, 12602–12610 (1990); European Patent Application 412,841 (Bang et al., published Feb. 13, 1991); and Nawa et al., *Thrombosis and Hemostasis*, 66, 366–370 (1992).

All such TM preparations are useful as long as they retain substantially the same ability to generate APC as do the naturally occurring forms of TM. That is, the modifications of TM, e.g., mutants, adducts, fragments, and other constructs, are useful in the methods and compositions of the present invention as long as they enhance the production of APC when used in combination with a cationic protein or modification thereof, as described above, according to the screening test outlined below. Specific preferred examples of TM preparations include isolated soluble forms of endogenous TM, recombinanfly produced extracellular domain forms of TM, and endothelial cell-expressed TM.

The thrombin can be any form of thrombin capable of combining with thrombomodulin and catalyzing the formation of APC. Examples include human, bovine, and porcine thrombin, and the like. Protein C is typically provided in its purified form. The purified protein C can be naturally occurring, synthetic, or recombinant. It can be a full length protein or a peptide fragment thereof. It can be an analog, i.e., mutant, of the naturally occurring protein, or a chemically modified adduct.

The anticoagulant compositions described above are useful in in vivo and in vitro applications. The compositions of the present invention are useful not only in the anticoagulant therapy of individuals having thrombotic conditions or in prophylactic applications, i.e., in in vivo applications, but are useful whenever inhibition of blood coagulation is required such as to prevent coagulation of stored whole blood and to prevent coagulation in other biological samples for testing or storage, i.e., in vitro applications. Thus, the cationic protein composition of this invention can be added to, or contacted with, any medium in which it is desired that blood coagulation be inhibited. Furthermore, the compositions of the present invention can be used to generate large amounts of APC either in vivo or in vitro (and harvested) for use in the treatment of disorders requiting infusion of APC.

The particularly preferred compositions of the present invention include those containing purified PF4, or a modification thereof, and a thrombomodulin preparation, such as purified soluble GAG+ thrombomodulin. Such compositions display particularly high levels of APC formation, and thus particularly effective levels of anticoagulation. For example, with the administration of a pharmacological form of TM, i.e., an exogenous form, in combination with purified naturally occurring or recombinant PF4, there is a 3–8 fold increase in the amount of APC formed, as compared to the administration of PF4 alone using endogenous forms of TM. This is particularly advantageous because TM and PF4, individually or together, have a higher therapeutic index than does heparin, which is currently used for anticoagulation therapy. Thus, a combination of TM and PF4 provides not only enhanced anticoagulation over either TM or PF4 used alone, but can be administered in higher dosages than heparin without adverse side effects.

Anticoagulant therapy is indicated for the treatment and prevention of a variety of thrombotic conditions, particularly coronary artery and cerebrovascular disease. Specific examples of clinical settings in which the compositions of the present invention can be used include treatment of myocardial infarction, pulmonary embolism, cerebrovascular disease, and the like. For example, they can be used in the treatment of venous thrombosis and thromboembolic disease, arterial thrombosis and thromboembolic disease, myocardial infarctions, pulmonary embolism, cerebrovascular disease, thrombotic occlusions during and subsequent to thrombolytic therapy or angioplastic therapy and, in general, any other such conditions for which anticoagulant therapy is indicated. Such conditions include, but are not limited to, thrombotic complications of other diseases, for example, cancer, tumor metastasis, diabetes, chronic inflammation, sepsis, shock, and other conditions where preventative or prophylactic anticoagulant effects are desired.

In one particular application, the anticoagulant compositions of the present invention can be administered along with conventional compositions used in thrombolitic therapy. For example, they can be administered along with urokinase, streptokinase, or tissue plasminogen activator. In this way blood clots can be dissolved by the thrombolitic compositions and further clotting can be avoided by the anticoagulant compositions of the present invention.

For these purposes, an effective amount of the cationic protein described above or a pharmaceutically acceptable salt thereof is administered to a patient in need thereof. By "effective amount" is meant that a quantity of one or more cationic proteins of the present invention (or a pharmaceutically acceptable salt or salts thereof) sufficient to alleviate the condition for which it is being administered is used. Preferably, an anticoagulant dose of the cationic protein is about 0.1 mg/kg to about 10 mg/kg of patient body weight per hour by infusion depending on, for example, the patient, and the severity of the thrombotic condition to be treated. The suitable dose for a particular patient can be readily determined. If used in combination with a TM preparation and/or THR, an "effective anticoagulant" dose of TM is preferably about 0.01–10 mg/kg of patient body weight per 6 hours, and more preferably about 0.1–1 mg/kg; an "effective anticoagulant" dose of THR is preferably about 0.1–2 units/kg of patient body weight per hour by infusion, and more preferably about 1–2 units/kg/hr; and an "effective anticoagulant" dose of protein C is preferably about 0.1–10 mg/kg or patient body weight per 6 hours. An effective anticoagulant amount of a composition containing one or more of these components is preferably an amount effective to provide the above-listed individual doses.

Although the cationic protein composition of this invention may be administered orally, parenteral administration is preferred. These modes of administration include, for example, subcutaneous, intravenous, intramuscular, and intraperitoneal. They also include administration by depot injection or by implant preparation formulated using polymers or synthetic silicones, for example, in such a manner as to permit a sustained release of the active ingredient. Preferably, the compositions of the present invention are administered intravenously.

The choice of pharmaceutically acceptable carrier for administration of the compositions is determined by the route of administration selected. For example, if the compositions are administered orally as by means of tablets, capsules, powders, suspensions, solutions, syrups and the like, such compositions utilize pharmaceutically acceptable carriers containing materials such as diluents, binders, lubricants, disintegrators, buffering agents, surfactants, emulsifying agents, dispersants, flavoring agents, and the like. For parenteral administration acceptable carriers include water, sesame oil, groundnut oil, aqueous propylene glycol, N,N'-dimethylformamide, and the like. Other oils that can be employed in these preparations are those of petroleum, animal, vegetable, or synthetic origin, for example, peanut oil, soybean oil, and mineral oil. For injectable compositions, water, saline, aqueous dextrose and related sugar solutions, ethanol, and glycols such as propylene glycol or polyethylene glycol are preferred carriers.

A particularly preferred carrier for the administration of the cationic proteins of the present invention, such as PF4, includes 10 mM sodium acetate (pH 5), 150 mM sodium chloride, and optionally human serum albumin. This formulation can be diluted with saline if desired.

The proteins can be administered in the form of pharmaceutically acceptable salts. These include, for example, acid addition salts derived from inorganic acids such as hydrochloric, phosphoric, phosphorous, nitric, sulfuric, hydrobromic, hydriodic acid and the like. Additionally, such salts can be derived from organic acids such as aliphatic mono and dicarboxylic acids, phenyl-substituted alkanoic acids, hydroxyalkanoic and alkandioic acids, for example. Therefore, such pharmaceutically acceptable salts include sulfate, bisulfate, chloride, bromide, iodide, fluoride, nitrate, phosphate, acetate, formate, propionate, caprate, fumarate, maleate, benzoate, chlorobenzoate, methylbenzoate, dinitrobenzoate, hydroxybenzoate, phthalate, benzenesulfonate, phenylacetate, phenylpropionate, citrate, malate, tartrate, and the like.

SCREENING TEST

For each type of cationic protein or modification thereof to be tested, 2 nM TM (full-length rabbit TM) and 500 nM protein C are incubated together in the presence of 1 mM (i.e., physiologic) $Ca^{2+}$ with either no cationic protein (for a baseline determination) or 10 μg/ml of the cationic protein. The generation of APC is initiated by the addition of 2 nM THR in 50 mM of the buffer Tris, 100 mM NaCl, pH 7.4 at 37° C. The reaction is allowed to proceed for 10 minutes, then quenched by the addition of AT III (antithrombin obtained from Enzyme Research Laboratories, Inc., South Bend, Ind.) and EDTA. APC can be quantified spectrophotometrically with the chromogenic substrate S-2366 (obtained from Kabi Vitrum, Franklin, Ohio) as described below in Example 1. A cationic protein that can be used in the methods and compositions of the present invention include those that show at least a two-fold increase in APC production, relative to a baseline of APC generated without the cationic protein.

A similar screening test can be used for various TM preparations using purified naturally occurring PF4. As with the cationic protein, a suitable TM preparation is one that shows at least a two-fold increase in APC production, relative to a baseline of APC generated without the PF4.

The invention will be further described by reference to the following detailed examples. These examples are offered to further illustrate the various specific and preferred embodiments and techniques. It should be understood, however, that many variations and modifications may be made while remaining within the scope of the present invention.

EXPERIMENTAL EXAMPLES

Example 1

APC Generation Using PF4 and Soluble Forms of TM

Human PF4 was purified from outdated platelets by THR, stimulation, $NH_4SO_4$ precipitation, heparin affinity chromatography, and Sephadex G-100 chromatography using a technique described in T. F. Deuel et al., *Proc. Natl. Acad. Sci. USA*, 74, 2256–2258 (1977), which is incorporated herein by reference. Dose-response studies were then performed with increasing amounts of PF4 to assay its effect upon the ability of three TM preps to generate APC from protein C. The three TM preps employed were: a) full-length rabbit TM purified from lungs (see, N. L. Esmon et al., *J. Biol. Chem.*, 257, 859–864 (1982)); and b) two differentially glycated versions of a recombinantly produced polypeptide fragment of human TM encompassing the entire extracellular domain ([amino acids 1–497], which includes the serine 492 glycosylation site) expressed in Chinese Hamster Ovary cells, provided by Berlex Biosciences (Richmond, Calif.). See, C. B. Glaser et al., *J. Clin. Invest.*, 90, 2565–2573 (1992). These polypeptides were produced in two chromatographically separable forms: the first has an apparent molecular weight of 116 kD and contains a chondroitinase ABC-cleavable GAG moiety (henceforth referred to as GAG+ TM); the second is an unglycated version of the same polypeptide with apparent molecular weight of 95 kD, henceforth referred to as GAG– TM.

Figure 1:
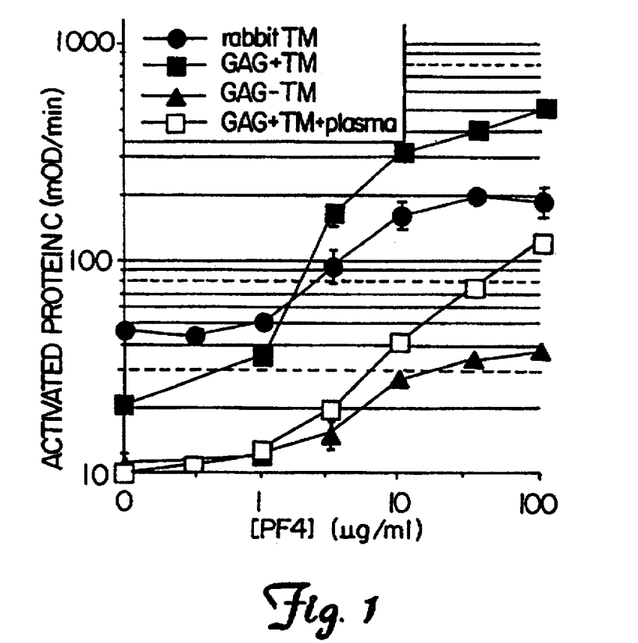
FIG. 1. A graph of the amount of APC generated by several forms of soluble TM upon the addition of PF4.

Instead of ablating the capacity of these TM constructs to generate APC as do the eosinophil cationic proteins, PF4 unexpectedly strikingly increased many-fold the rate of APC generation, even in the presence of plasma. See FIG. 1. For each type of TM, 2 nM TM and 500 nM protein C were incubated together in the presence of 1 mM (i.e., physiologic) $Ca^{2+}$ with or without PF4, and the generation of APC initiated by the addition of 2 nM THR in 50 mM Tris, 100 mM NaCl, pH 7.4 at 37° C. The reaction was allowed to proceed for 10 minutes, then quenched by the addition of AT III (obtained from Enzyme Research Laboratories, Inc., South Bend, Ind.) and EDTA. APC was quantified spectrophotometrically with the chromogenic substrate S-2366 (obtained from Kabi Vitrum, Franklin, Ohio). The spectrophotometric analysis involved the conversion of the chromogenic substrate at 405 nM in a 37° C. spectrophotometer cell based on the initial rate of optical density change. Negative controls of plastic wells treated in a parallel fashion except that TM was omitted. Values obtained from these controls were then subtracted from the rates measured for wells containing monolayers.

PF4 accelerates APC generation by full-length rabbit TM and GAG– TM 4-fold, and that of GAG+ TM 25-fold. GAG+ TM was also accelerated 10-fold by PF4 in the presence of 15% defibrinated plasma. Thus, on a "fold-over-baseline" comparison basis, the GAG+ form of TM is accelerated by PF4 more than six times as much as are full-length rabbit TM and GAG– TM. Even on a molar basis, despite having less than half the activity of rabbit TM in the absence of PF4, GAG+ TM has nearly three times the activity of rabbit TM in the presence 100 μg/ml PF4. Pertinent controls (not shown) demonstrated that PF4 has essentially no effect upon the TM-independent activation of protein C by THR. Similarly, neither PF4 alone nor PF4 together with TM generated APC in the absence of added THR. The increase in APC was not an artifact of PF4 influencing the catalytic activity of APC towards chromogenic substrate. These results demonstrated a pronounced acceleratory effect of PF4 upon the ability of THR/TM complex to generate APC that is powerfully enhanced by the presence on TM of the GAG moiety. Although the results shown in FIG. 1 were obtained using purified native, i.e., naturally occurring, PF4, recombinant PF4 produced similar results.

Figure 2:
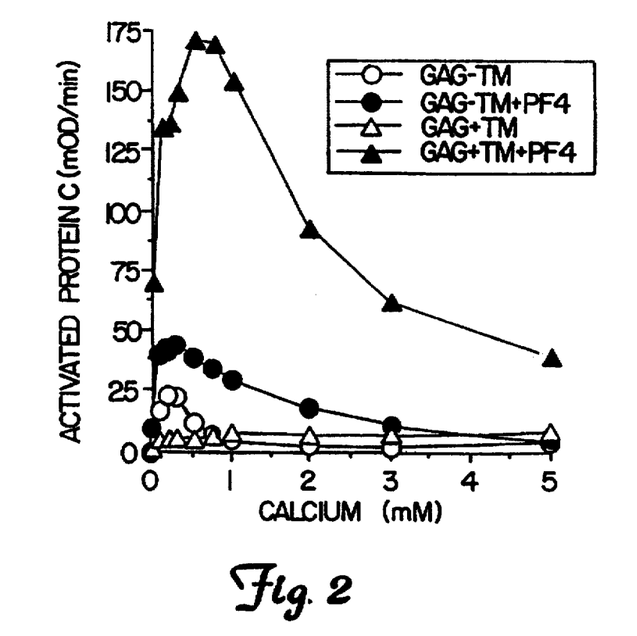
FIG. 2. A graph of the amount of APC generated by TM upon the addition of PF4 and several concentrations of calcium.

An obvious initial hypothesis to explain the above observations is that PF4, which binds strongly to heparin as well as to other GAGs, similarly interacts with TM by binding to the GAG domain. Because presence or absence of this GAG domain has a pronounced effect upon the $[Ca^{2+}]$-dependence profile of TM APC generation, it was ascertained whether addition of PF4 to GAG+ TM ablates this GAG influence and converts its $[Ca^{2+}]$-dependence to resemble that of the GAG– form. As shown in FIG. 2, in the absence of added PF4, GAG+ and GAG– forms of TM have, as expected, strikingly different $[Ca^{2+}]$-dependence curves: GAG+ TM activity increases progressively with increasing $Ca^{2+}$ concentration whereas GAG– TM activity has an optimum at subphysiologic $Ca^{2+}$ (0.3 mM $Ca^{2+}$). Addition of PF4 to the GAG variant increases APC generation at all $Ca^{2+}$ concentrations but does not shift the overall shape of the curve. By contrast, addition of PF4 to the GAG+ variant not only greatly accelerates APC generation, but also converts its $Ca^{2+}$ dependence profile to resemble that of the GAG– variant with an optimum of 0.5 mM. Furthermore, adding PF4 allows both the GAG+ and GAG– forms of TM to generate APC even in the absence of $Ca^{2+}$ (for the 0 calcium point, the buffers were supplemented with 1 mM EDTA).

Previous work by Kurosawa et al., *J. Biol. Chem.*, 262, 2206–2212 (1987), has shown that the peculiar, low-calcium optimum of APC generation by one GAG– form of TM—elastase-cleaved TM—is only seen in the presence of PC that is post-translationally modified by a vitamin K-dependent process to contain a γ-carboxyglutamic acid domain (Gla domain). If this Gla domain is removed proteolytically, then the resulting Gla-domainless PC in combination with elastase-cleaved (GAG–) TM shows an APC generation calcium dependence identical to that of the GAG+ TM. Therefore, if PF4 interacts with GAG+ TM to functionally "de-GAG" it—a hypothesis suggested by FIG. 2—the marked acceleration of APC generation that occurs with native PC should not be seen in the presence of Gla-domainless PC. As shown in Table 1, this is precisely the case. This finding clearly implicates the Gla-domain of protein C in the marked acceleratory effect of PF4 upon APC generation by GAG+ forms of TM.

TABLE 1

Role of the protein C Gla-domain in PF4
acceleration of TM APC generation
APC generated (mOD/min)

| TM preparation | Protein C | Gla-domainless protein C |
|---|---|---|
| GAG + TM | 5.7 ± 1.5 | 9.5 ± 2.3 |
| GAG + TM + 33 µg/ml PF4 | 114 ± 7.6 | 4.2 ± 1.4 |

Example 2

APC Generation Using Endothelial Cell Monolayers

Figure 3:
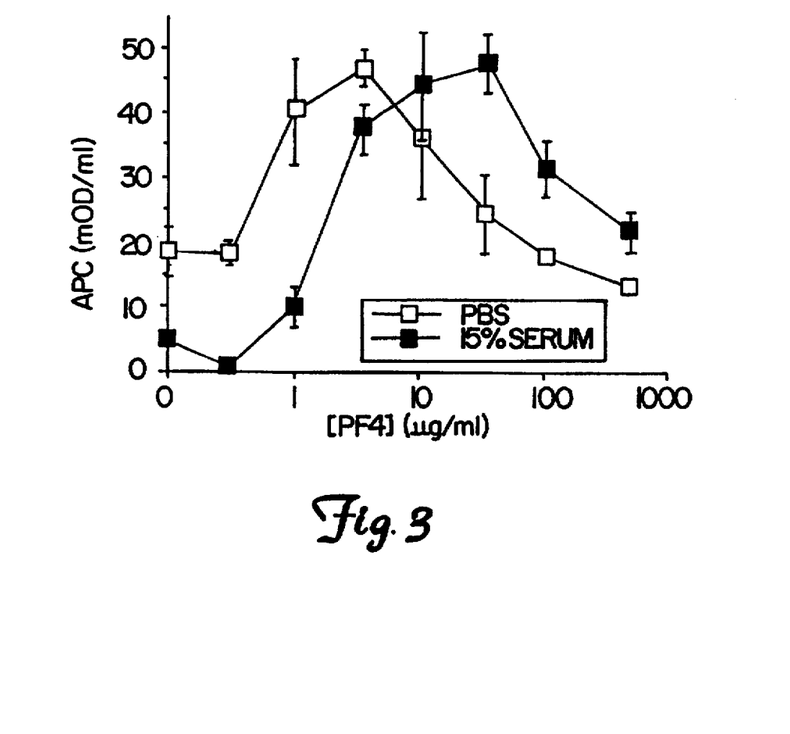
FIG. 3. A graph of the amount of APC generated by porcine aortic endothelial monolayers.

In addition to stimulating APC generation by soluble forms of TM in buffers, PF4 also stimulates APC generation of cell-surface TM on porcine aortic endothelial cell (PAEC) monolayers in plasmatic conditions. See FIG. 3. In these experiments, 1 cm$^2$ monolayers of endothelial cells were overlaid with PBS buffer containing 500 nM PC and 1 mM Ca$^{2+}$, then further supplemented with either PBS or PBS with 15% (v/v) bovine serum. To these wells were then added increasing concentrations of purified native PF4. The resultant mixture was incubated for 20 minutes after which either 2 nM (PBS) or 10 nM THR (15% serum) was added and the generation of APC allowed to proceed for 45 minutes prior to quenching with addition of AT III and EDTA. Supernatants were then centrifuged to remove cellular debris and APC generation quantified using chromogenic substrate S-2366 as described above. In the absence of added serum, there is a 2½-fold increase in APC generation with an optimum at 3.3 µg/ml of PF4, but decreasing APC generation with higher concentrations. In contrast, in the presence of 15% serum, the baseline APC generation is much lower despite the presence of higher concentrations of THR. There is a PF4 dose-dependent increase in APC generation with an optimum at 33 µg/ml PF4, at which point APC generation is 10-fold higher than baseline. In considering explanations for this phenomenon other than accelerated APC generation, we find that addition of PF4 to known amounts of APC added to 15% serum did not diminish or augment APC detection by chromogenic substrate, thus ruling out a substantive contribution to this phenomenon by protein C inhibitors in serum (not shown). Another potential explanation for the acceleration of APC generation by monolayers in the presence of serum is that PF4 might reverse accelerated AT III/thrombin interactions caused by heparin sulfate-like molecules on endothelial cell surfaces, a described phenomenon. However, regardless of the ultimate explanation for this phenomenon, the net result remaing that PF4 accelerates 10-fold endothelial-dependent generation of the potent natural anticoagulant, activated protein C, under plasmatic conditions. Although the results shown in FIG. 3 were obtained using purified naturally occurring PF4, recombinant PF4 produced similar results.

Although the Inventors do not wish to be held to any particular theory, it is believed that PF4 released by activated platelets binds to circulating and endothelial TM through an electrostatic interaction with the polyanionic GAG domain. Unlike cationic eosinophil granule proteins, however, PF4 produces a conformational change in the TM molecule that greatly accelerates thrombin/TM complex catalysis of APC formation. This acceleration of APC catalysis, in turn, reflects a large decrease in the $K_m$ of the THR/FM complex for protein C, a consequence of conformational changes both in the THR-TM complex and in protein C itself through interactions of PF4 with the Gla-domain of protein C. The net result is that, in the presence of circulating THR, PF4 from activated platelets amplifies production of APC by endothelial and circulating forms of TM, thereby generating a potent natural anticoagulant that restricts unregulated propagation of thrombosis.

Example 3

APC Generation Using Poly-L-Lysine and Protamine Sulfate

Figure 4:
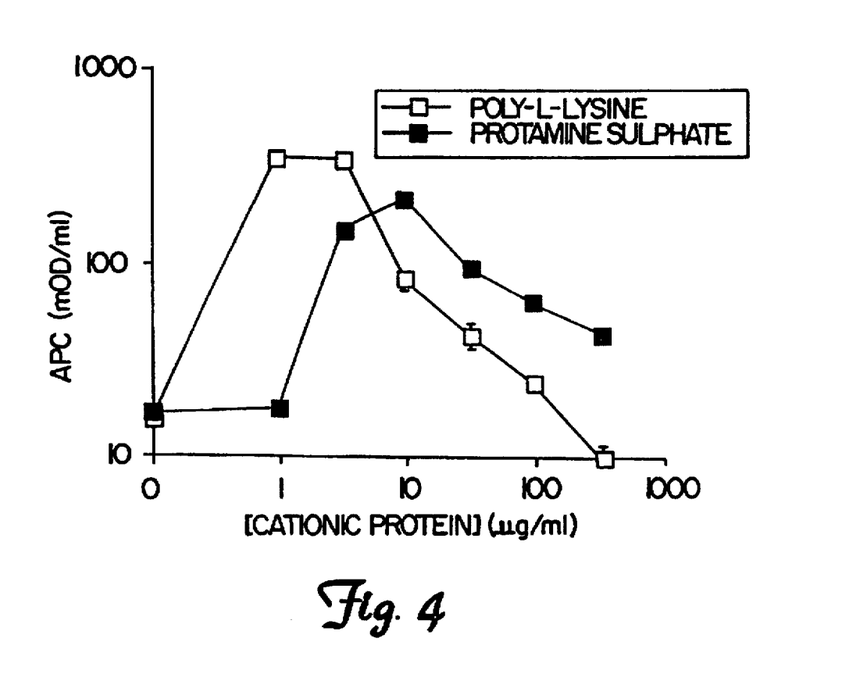
FIG. 4. A graph of the amount of APC generated by soluble TM upon the addition of poly-L-lysine or protamine sulfate.

As shown in FIG. 4, the acceleratory effect of PF4 upon APC generation by thrombomodulin can be replicated by two other cationic proteins, poly-L-lysine (molecular weight 4000–15,000 obtained from Sigma Chemical, St. Louis, Mo.) and protamine sulfate (molecular weight 5000–15,000 obtained from Sigma Chemical, St. Louis, Mo.). The conditions used were identical to those listed in Example 1 except GAG+ TM obtained from Berlex Biosciences was used for all experiments. When full-length rabbit TM was employed instead of GAG+ TM, a 2.5-fold acceleratory effect of these cationic proteins was seen (data not shown). It is believed that this amplification of TM-dependent APC generation by poly-L-lysine and protamine sulfate is attributable to the cationic nature of these substances because no such effect is seen in the presence of the anionic proteins albumin and thrombospondin and the polyanionic GAGs heparin, chondroitin surlate A, and chondroitin sulfate E.

The complete disclosure of all patents, patent documents, and publications cited herein are incorporated by reference. The foregoing detailed description and examples have been given for clarity of understanding only. No unnecessary limitations are to be understood therefrom. The invention is not limited to the exact details shown and described, the exact details shown and described, for variations obvious to one skilled in the art will be included within the invention defined by the claims.

What is claimed is:

1. A method of inhibiting blood coagulation in a patient comprising administering to the patient an effective anticoagulant amount of a cationic protein selected from the group consisting of Platelet Factor 4, poly-L-lysine and protamine sulfate while maintaining a physiological Ca$^{2+}$ concentration in the patient.

2. The method of claim 1 wherein the cationic protein is purified naturally occurring Platelet Factor 4 or purified recombinant Platelet Factor 4.

3. The method of claim 1 wherein the cationic protein is poly-L-lysine.

4. The method of claim 1 wherein the cationic protein is protamine sulfate.

5. The method of claim 1 further comprising administering a thrombomodulin preparation.

6. The method of claim 5 wherein the thrombomodulin is a purified soluble GAG+ form of thrombomodulin.

7. The method of claim 5 further comprising administering thrombin.

8. The method of claim 1 further comprising administering thrombin.

9. A method of producing activated protein C in a patient comprising administering to the patient an effective amount of a cationic protein selected from the group consisting of Platelet Factor 4, poly-L-lysine and protamine sulfate while maintaining a physiological $Ca^{2+}$ concentration in the patient.

10. The method of claim 9 wherein the patient has septic shock.

11. The method of claim 9 wherein the cationic protein is purified naturally occurring Platelet Factor 4 or purified recombinant Platelet Factor 4.

12. The method of claim 9 wherein the cationic protein is poly-L-lysine or protamine sulfate.

13. The method of claim 9 further comprising administering a thrombomodulin preparation.

14. The method of claim 13 wherein the thrombomodulin is a purified soluble GAG+ form of thrombomodulin.

15. The method of claim 13 further comprising administering thrombin.

16. The method of claim 9 further comprising administering thrombin.

* * * * *